United States Patent [19]

Verbrugge et al.

[11] 4,012,430
[45] Mar. 15, 1977

[54] PROCESS FOR THE PREPARATION OF CYCLOPROPANE DERIVATIVES

[75] Inventors: Pieter A. Verbrugge; Elisabeth W. Uurbanus, both of Amsterdam, Netherlands

[73] Assignee: Shell Oil Company, Houston, Tex.

[22] Filed: June 17, 1975

[21] Appl. No.: 587,574

Related U.S. Application Data

[63] Continuation-in-part of Ser. Nos. 359,930, May 14, 1973, abandoned, and Ser. No. 359,931, May 14, 1973, Pat. No. 3,917,667.

[30] Foreign Application Priority Data

May 16, 1972 United Kingdom ............ 22911/72

[52] U.S. Cl. .................... 260/468 H; 260/557 R;
   260/469; 260/558 R; 260/648 D
[51] Int. Cl.$^2$ ................. C07C 67/30; C07C 102/00
[58] Field of Search ....... 260/648 D, 468 H, 557 R, 260/469, 558 R

[56] References Cited

UNITED STATES PATENTS

| 3,359,252 | 12/1967 | Nerdel et al. | 260/648 D |
| 3,363,012 | 1/1968 | Norell et al. | 260/648 D |

FOREIGN PATENTS OR APPLICATIONS

| 1,005,641 | 9/1965 | United Kingdom | 260/468 H |
| 1,227,144 | 4/1971 | United Kingdom | |
| 1,323,183 | 7/1973 | United Kingdom | 260/468 H |

OTHER PUBLICATIONS

Richter, Organic Chemistry, vol. 1, pp. 205–206 (1934).
Kajigaeski, Tetrahedron Letters, 51, pp. 4887–4888 (1971).
Makosza, Tetrahedron Letters, 53, pp. 4659–4662 (1969).

*Primary Examiner*—Lorraine A. Weinberger
*Assistant Examiner*—Michael Shippen

[57] ABSTRACT gem-dihalocyclopropane derivatives are prepared by reacting olefinic compounds with a dihalocarbene in the presence of an improved catalyst.

8 Claims, No Drawings

4,012,430

PROCESS FOR THE PREPARATION OF CYCLOPROPANE DERIVATIVES

CROSS-REFERENCE TO RELATED-APPLICATIONS

This application is a continuation-in-part of Serial No. 359,930 now abandoned and Serial No. 359,931, now U.S. Patent No. 3,917,667 both filed on May 14, 1973.

BACKGROUND OF THE INVENTION

There is a strong evidence (see page 36 "Divalent Carbon" by Jack Hine, The Ronald Press Comp., New York, 1964) that upon treatment with an aqueous solution of a strong base a haloform undergoes the following reactions to give the reactive intermediate dihalocarbene (dihalomethylene):

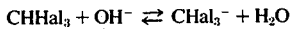

In the above equations Hal represents a halogen atom. The dihalomethylene readily reacts with water to form carbon monoxide and hydrogen halide.

Makosza et al (see Tetrahedron Letters 53 (1969) 4659–62) have contacted aqueous sodium hydroxide with chloroform containing an olefin in the presence of a catalytic amount of triethylbenzylammonium chloride. They found that the corresponding gem-dichlorocyclopropane derivative was formed:

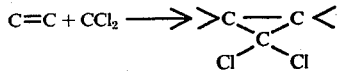

SUMMARY OF THE INVENTION

New and improved catalysts for the reaction of olefinic compounds with dihalocarbenes have now been discovered. The invention accordingly can be generically defined as: in the preparation of gem-dihalocyclopropane derivatives by contacting an aqueous phase containing an alkali metal hydroxide and an organic phase containing both a haloform and an olefinic compound in the presence of a cataylst, the improvement which comprises employing as the catalyst a quaternary onium compound of the formula

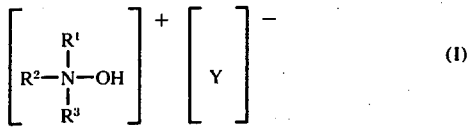

in which $R^1$, $R^2$ and $R^3$ eacy is alkyl or cycloalkyl of up to 40 carbon atoms and Y is a hydroxide or other anion. Repesentative examples of such compounds are shown in Richter's Organic Chemistry, Vol I, page 205, Nordemann Publishing Co., Inc., New York (1934).

High yields of gem-dihalocyclopropane derivatives are often obtained when the onium compounds of formula I are employed as catalysts.

Examples of the onium salts which may be used are iodides, bromides, chlorides, fluorides, alkyl sulfates, tetrafluoroborates and hydrocarbon arylsulfonates, such as tosylates.

$R^1$, $R^2$ and $R^3$ in formula I may be straight-chain or branched-chain alkyl or cycloalkyl, of up to, for example, 40 carbon atoms each, preferably up to 20 carbon atoms each. The three alkyl groups may be the same, two may be the same and the third different or the three groups may all be different. Examples of vary active catalysts are trimethylhydroxylammonium hydroxide, methyldiethylhydroxylammonium iodide, methyldiethylhydroxylammonium iodide and triethylhydroxylammonium hydroxide.

The catalysts used in the process according to the present invention may be added to the aqueous and/or organic phase or may be found in situ. Examples included later herein illustrate in situ preparation. Quaternary onium compounds of formula I can be prepared in situ starting from a (cyclo)aliphatic tertiary amine and hydrogen peroxide, from a di(cyclo)alkylhydroxyl amine and an alkyl iodide or by hydration of a (cyclo)aliphatic tertiary amine oxide.

A physical mixture of any one of the above-mentioned onium compounds may be used as the catalyst. It is possible to use a compound having two or more of the onium structures mentioned in formula I in one molecule.

$R^1$, $R^2$ and $R^3$ may represent substituted hydrocarbyl groups. A hydroxyl group is an example of a substituent.

Ethylenically unsaturated compounds, generally, react with dihalomethylenes generated in situ to form gem-dihalocyclopropane derivatives. This reaction may be represented by means of the following equation:

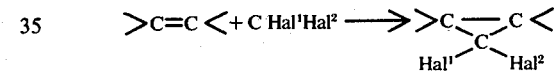

in which $Hal^1$ and $Hal^2$ each represent a halogen atom. $Hal^1$ and $Hal^2$ may be the same or different. Examples of ethylenically unsaturated compounds which may be used are:

1. straight and branched alkenes with terminal double bonds, such as ethene, propene, 1-butene, 1-pentene, 1-hexene, 1-heptene, 1-octene, 3-methyl-1-butene, 3-methyl-1-hexene, 1-decene and 1-alkenes with more than 10 carbon atoms per molecule.

2. 2-alkenes, 3-alkenes and alkenes in which the double bond is even futher removed from a terminal carbon atom, for example 2-pentene, 2-hexene, 3-heptene, 2-methyl-2-butene, 2-octene, 3-nonene and internal alkenes with 10 or more carbon atoms per molecule.

3. di-, tri- and polyalkenes; these alkenes may be conjugated or non-conjugated. For example, butadiene is converted into 2,2,2',2'-tetrachlorobicyclopropyl; other examples of starting compounds are norbornadiene and hexamethyldewarbenzene.

4. cyclic ethylenically unsaturated compounds having a carbon-carbon double bond in the ring; very good results have been obtained with cycloalkenes, particularly with cyclohexene, which is converted into 7,7-dihalonorcarane.

5. substituted ethylenically unsaturated compounds. Examples of substituents are: (a) aromatic groups: phenyl or naphthyl groups, whether or not substituted, such as in styrene (converted into 1,1-dihalo-2-phenylcyclopropane), alphamethylstyrene (converted into 1,1-dihalo-2-phenyl-2-methylcyclopropane), trans-trans-diphenylbutadiene-1,3, , tetraphenylbutadiene (which takes up two dihalomethylene groups), cyclooctatetraene (converted into 9,9-dichloro-bicyclo(6,1,0-nonatriene-(2,4,6)), trans-stilbene (converted into 1,1-dihalo-2,3-diphenylcyclopropane), and cyclododecatriene. (b) halogen atoms: fluorine, chlorine, bromine and iodine atoms; (c) alkoxy groups: butoxyethene (converted into 1,1-dihalo-2-butoxycyclopropane) and 2-propoxypropene (converted into gem-dichloro-2-methyl-2-propoxycyclopropane).

It has been found that alkenecarboxylic acids form an exception to the general rule, in that the base used to generate the dihalocarbene attacks the alpha-hydrogen atom or alkyl moiety (bonded to the carbon atom bearing the carboxyl moiety) to give products other than that desired. To prepare gem-dihalocyclopropanecarboxylic acids from such acids, it is necessary to use an ester or amide thereof, then convert the resulting gem-dihalocyclopropanecarboxylic acid ester or amide to the acid.

Thus, gem-dihalocyclopropanecarboxylic acids can be prepared by reaction of a dihalocarbene with (a) a tertiary-alkyl ester of an alpha-unsubstituted alkenecarboxylic acid, (b) an N-substituted amide of an alpha-unsubstituted alkenecarboxylic acid, (c) an alkyl ester of an alpha-(alkyl-substituted)alkenecarboxylic acid, or (d) an N-substituted amide of an alpha-(alkyl-substituted)alkenecarboxylic acid, to form the corresponding ester or amide of a gem-dihalocyclopropanecarboxylic acid. The free acid can then be obtained by pyrolysis of the ester or acid hydrolysis of the amide, if desired; however, in some cases a desired cyclopropane ester or amide can be prepared directly from the appropriate alkenecarboxylic acid ester or amide.

Accordingly, this invention also includes a process for preparing esters and amides of gem-dihalocyclopropanecarboxylic acids which comprises contacting an aqueous phase containing an alkali metal hydroxide and an organic phase containing both a haloform and an alkenecarboxylic acid derivative which is one of:

a. tertiary-alkyl esters of alpha-unsubstituted alkenecarboxylic acids;

b. alkyl esters of alpha-(alkyl-substituted) alkenecarboxylic acids; and d. N-substituted amides of alkenecarboxylic acids; in the presence of, as catalyst, at least one of certain onium compounds as hereinbefore described.

While the process of the invention appears to be applicable to conversion of any alkenecarboxylic acid

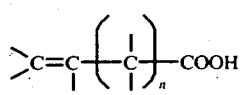

wherein $n = 0$ or a whole member, and the free valence bonds may be satisfied by hydrogen or any substituent not reactive with strong base and/or dihalocarbene, the process of this invention is of particular interest (because of biological activity of the gem-dihalocyclopropanecarboxylic acid or derivative prepared therefrom) for conversion of acrylic acids of the general formula:

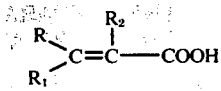

wherein R is hydrogen, alkyl or phenyl and $R_1$ and $R_2$ each independently is hydrogen or alkyl.

According to this invention an ester or amide of the alkenecarboxylic acid is employed. If the acid is alpha-unsubstituted — $R_2$ is hydrogen — then a tertiary-alkyl ester is employed. If the acid is alpha-substituted — $R_2$ is alkyl — then any alkyl ester is suitable. For either type of acid, an N-substituted amide can be employed. Preparation of the necessary ester can be accomplished by known esterification procedures. Examples of suitable esters are esters of tert-butyl alcohol; 2-methyl-2-butanol; 3-methyl-3-pentanol; 1-alkylcycloalkanols; such as 1-methyl-cyclopentanol and 1-methylcyclohexanol. Suitably the ester group contains up to 20 carbon atoms, preferably to to 10 carbon atoms. Particularly suitable are the tertiary-butyl esters.

In the amides, suitable substituents on the nitrogen atom are, for example, lower alkyl, cycloalkyl, aryl, aralkyl and alkaryl groups. The nitrogen atoms may form part of a hetero-aromatic systems, and, if desired, inert substituents may also be present. There may be one or two substituents on the nitrogen atom. The alkyl groups may be primary, secondary or tertiary. Tertiary hydrocarbyl groups, particularly tertiary alkyl groups are suitable as substituent. Excellent results have been obtained with N-tert-butyl-substituted carboxamides. Other examples of suitable tertiary alkyl groups are 2-methyl-2-butyl and 3-methyl-3-pentyl groups and those derived from alkylcycloalkanes, for instance from methylcyclohexane. For example, N-tert-butyl beta-methylcrotonamide is converted with a very good yield into N-tert-butyl-2,2-dichloro-3,3-dimethylcyclopropane amide. An example of an N-cycloalkyl substituted carboxamide is N-1-adamantyl-beta-methylcrotonamide, which is converted with a very good yield into N-1-adamantyl-2,2-dichloro-3,3-dimethylcyclopropanecarboxamide. Suitably each substituent on the nitrogen atom contains up to 20 carbon atoms, preferably up to 10 carbon atoms.

Such amides are readily prepared by method known in the art. Typically methods for preparing such amides are described hereinbefore for the prepartion of N-tert-butyl-beta-methylcrotonamide.

Conversion of the ester or amide may be effected by simply mixing: (a) the ester or amide, (b) a haloform, (c) an aqueous alkali metal hydroxide and (d) the catalyst, the mixing being conducted for a sufficient time to permit the reaction to go to completion.

Also, ethylenically unsaturated compounds having both a carbonitrile group and a (alpha) hydrogen atom bonded to the same double-bonded carbon atom of the ethylene moiety almost do not form gem-dihalocyclopropane derivatives, but form black high molecular weight tar-like products. The corresponding olefins not having an alpha-hydrogen atom, instead having an alkyl or cycloalkyl group bonded to the alpha-carbon atom, readily form the corresponding gem-dihalocyclopropane carboxylic and derivatives.

The haloform which is used has the general formula

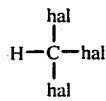

in which each hal represents a halogen atom, viz. a fluorine, chlorine, bromine or iodine atom. The halogen atoms present in the haloform may be the same or different; they may be present in all possible combinations. Examples of haloforms are $CHF_3$, $CHF_2Cl$, $CHFCl_2$, $CHCl_3$, $CHIBr_2$ and $CHClBrI$. Very good results have been obtained with $CHCl_3$.

The aqueous alkali metal hydroxide is preferably a strong aqueous solution with a concentration of preferably at least 30% by weight and in particular of at least 40% by weight alkali metal hydroxide. The maximum concentration of the alkali metal hydroxide in the solution is the concentration of a saturated solution at the temperature at which the process is effected. Solid alkali metal hydroxide may be present. the alkali metal hydroxides which are used, are those of lithium, sodium, potassium, rubidium and cesium. Very good results have been obtained with aqueous sodium hydroxide having a concentration of at least 45% by weight.

Conversion of the olefinic compound to the gem-dihalocyclopropane compounds may be effected by simply mixing: (a) the olefinic compound, (b) a haloform, (c) an aqueous alkali metal hydroxide, and (d) the catalyst; the mixing being conducted for a sufficient time to permit the reaction to go to completion. The mixing should be vigorous, because this improves the yield of, and the selectivity of conversion of the olefinic compound to, the desired gem-dihalocyclopropane derivative. In most cases, conversion will be complete in about one to about five hours time.

Suitably the conversion may be conducted at temperatures within the range of from about 0° C to about 200° C. Ordinarily it will be found to be desirable that the conversion be carried out at a temperature of at least 20° C, but below about 100° C, with mildly elevated temperatures — say from 30°–60° C — being about optimum from the practical conduct of the conversion.

The process is conveniently carried out at atmospheric pressure.

The molar ratio in which the haloform and the olefinic compound and the molar ratio in which the haloform and the alkali metal hydroxide are employed may vary within a wide range and are not critical. The more haloform and the more alkali metal hydroxide are used, relatively, the more rapid the reaction proceeds. Preferably the olefin/haloform molar ratio lies between 1:1 and 1:20, while the preferred haloform/alkali metal hydroxide molar ratio is between 1:1 and 1:10. Molar ratios outside the preferred two ranges are not excluded.

The catalyst is usually employed in an amount which may be indicated by the expression "catalytic amount". The minimum amount of catalyst is that amount which gives the smallest noticeable catalytic effect. The catalyst/haloform molar ratio is preferably between 1:10 and 1:10,000, but molar ratios 1:<10 and 1:<10,000 are not excluded. Excellent results have been obtained with catalyst/haloform molar ratios between 1:100 and 1:1000.

The process may be effected in the presence or in the absence of a solvent. Suitable solvents are: n-alkanes, for example n-pentane, n-hexane and n-heptane; ethers, for example ethers with straight alkyl groups, in particular diethylether, and cyclic ethers, in particular dioxane. The solvents may be used in an amount ranging within wide limits, for example in a haloform/solvent weight ratio in the range between 0.1:1 and 20:1. Weight ratios outside this range are not excluded. Chlorinated hydrocarbons, in particular dihalomethanes, are particularly useful solvents, because they lead to a considerable increase of the yield of gem-dihalocyclopropane derivatives. With dichloromethane yields of 100% or nearly 100% have been obtained.

Since the gem-dihalocyclopropane product is essentially insoluble in the aqueous phase of the final reaction mixture, the product can be recovered by phase separation and recovery from the organic phase by orthodox techniques, such as evaporation of the solvent, followed by recrystallization from a suitable liquid; by extraction of the organic phase with a selective solvent (such as ether) for the product. If, because of the physical character of the final reaction mixture, phase separation does not appear feasible (the final mixture is an apparently intractable emulsion, or the like), the product may be recovered by extraction of the mixture with a suitable selective solvent such as ether.

Conduct of the process of the invention in specific cases is shown in the following examples:

EXAMPLE I

In a flask provided with a one-blade paddle mixer, a mixture of 1.64 grams of cyclohexene, 23.7 grams of chloroform, 20 milliliters of 50%w aqueous sodium hydroxide, 5 milliliters of dichloromethane, 1 milliliter of n-octane (to serve as a GLC marker) and 0.010 gram of the catalyst indicated in Table I was stirred vigorously at 40° C. Samples were taken after stirring had been started at the times indicated in Table I. Table I presents the yields of 7,7-dichloronorcarane. The selectivity to the latter compound was 100% in all cases. A dash indicates that no analysis was effected.

TABLE I

| Catalyst | Yield of 7,7-dichloronorcarane, %, after hours | | | |
|---|---|---|---|---|
| | 0.5 | 1 | 2 | 3 |
| trimethylhydroxyammonium hydroxide | — | 100 | — | — |
| triethylhydroxyammonium hydroxide | — | — | — | 100 |
| diethylmethylhydroxyammonium iodide | — | — | 100 | — |

Triethylamine oxide and diethylmethylhydroxyammonium iodide were prepared in situ starting triethylamine and 30l% by weight aqueous hydrogen peroxide, and hydroxydiethylamine and methyl iodide.

EXAMPLE II

In a flask provided with a one-blade paddle mixer, a mixturwe of 1 g of benzyl-beta-methylcrotonate, 24 grams of chloroform, 5 milliliters of dichloromethane, 1 milliliter of n-octane, 10 milliliters of 50% aqueous sodium hydroxide and 0.010 gram of catalyst was stirred vigorously at a temperature of 40° C. Table II presents the conversion and selectivity to benzyl 2,2-dichloro-3,3-dimethyl cyclopropanecarboxylate, measured at four different times after the start of the experiment.

TABLE II

| Catalyst | Yield of benzyl 2,2-dichloro-3,3-dimethylcyclopropanecarboxylate, after hours | | | Formation of byproducts |
|---|---|---|---|---|
| | 0.5 | 1 | 2 | |
| trimethylhydroxyl-ammonium hydroxide | 33 | 50 | — | started after 1 hour |

The process provided by this invention is particularly of interest for preparing fungicidally and insecticidally active gem-dihalocyclopropane derivatives of the formula

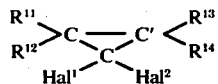

wherein Hal¹ and Hal² each is halogen atom; $R^{11}$ is hydrogen or alkyl or phenyl group; $R^{12}$ and $R^{13}$ each is hydrogen or alkyl group; and $R^{14}$ is carbonitrile (when $R^{13}$ is alkyl). These fungicidally active compounds are especially active against fungal diseases of rice crops, in particular against rice blast (pyricularia oryzae). These compounds and their utility are described in German Pat. No. 2,219,710).

Application of the process of this invention for the preparation of a particular pesticidally active compound is demonstrated and exemplified by the preparation of 2,2-dichloro-3,3-dimethylcyclopropanecarboxylic acid. First, beta-methylcrotononitrile is prepared, for example, by reacting methallyl chloride and sodium cyanide or by reacting isobutyraldehyde and hydrogen cyanide followed by dehydration of the 2-hydroxy-3-methylbutanenitrile formed. Then, beta-methylcrotononitrile is converted into N-tert-butyl-beta-methylcrotonamide according to the reaction of J. J. Ritter (Chapter 3, "Organic Reactions," Volume 17, 1969, John Wiley & Sons, Inc., New York) by reaction with isobutene in the presence of concentrated sulfuric acid followed by dilution with water. Addition of dichlorocarbene (dichloromethylene) to the latter amide according to the process of this invention yields N-(tert-butyl)-2,2-dichloro-3,3-dimethylcyclopropanecarboxamide, which is easily converted into the corresponding carboxylic acid (and the corresponding acid salt of an amine) by heating in a mineral acid, such as concentrated hydrochloric acid. The carboxylic acid crystallizes upon cooling and may be isolated by filtration. If desired, the amine simultaneously formed may be recovered from the filtrate.

The pesticidal acid can also be prepared by reacting dichloromethylene with the tert-butyl ester of beta-methylcrotonic acid to form the tert-butyl ester of 2,2-dichloro-3,3-dimethylcyclopropanecarboxylic acid. The acid per se is readily obtained by heating the ester at a temperature in the range of about 200° to about 250° C. (For example, this ester is completely converted to the acid when heated for ten minutes at 210° C.) The by-product of the pyrolysis is the appropriate alkene — in the case of the tert-butyl ester, the alkene is isobutene. (Which, of course, could be re-cycled to prepare more of the N-tert-butyl-beta-methylcrotonamide precursor.

What is claimed is:
1. A process for preparing esters and amides of gem-dihalocyclopropanecarboxylic acids which comprises contacting an aqueous phase containing an alkali metal hydroxide and an organic phase containing both a haloform and an alkenecarboxylic acid derivative of the formula

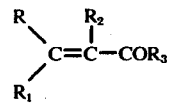

wherein R is hydrogen, alkyl or phenyl and $R_1$ and $R_2$ each independently is hydrogen or alkyl, $R_3$ is alkyloxy or substituted amino with the proviso that when $R_2$ is hydrogen, $R_3$ is only tert-alkyloxy or substituted amino, in the presence of as catalyst a quaternary onium compound of the formula

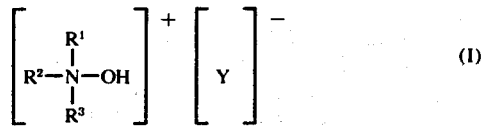

in which $R^1$, $R^2$ and $R^3$ each is alkyl or cycloalkyl of up to 40 carbon atoms and Y is an anion selected from hydroxide, iodide, bromide, chloride, fluoride, alkyl sulfate, tetrafluoroborate or tosylate.

2. The process according to claim 1 wherein the reaction is conducted in the presence of a chlorinated hydrocarbon as a solvent.

3. The process according to claim 2 in which the solvent is dichloromethane.

4. A process according to claim 1 wherein the ester or amide is that of a crotonic acid.

5. A process according to claim 1 wherein the onium compound has 1 to 2 carbon atoms in each alkyl.

6. A process according to claim 4 wherein the alkenecarboxylic acid derivative is an amide and is N-tert-butylmethylcrotonamide.

7. A process according to claim 4 wherein the alkenecarboxylic acid derivative is an ester and is tert-butyl betamethylcrotonate.

8. A process according to claim 1 wherein the catalyst and the haloform are applied in a molar ratio of between 1:10 to 1:10,000.

* * * * *